United States Patent
Kim et al.

(10) Patent No.: US 10,039,446 B2
(45) Date of Patent: Aug. 7, 2018

(54) METHOD FOR DETECTING DEFECTIVE ZONE OF RETINAL NERVE FIBER LAYER

(71) Applicants: NATIONAL CANCER CENTER, Gyeonggi-do (KR); SEOUL NATIONAL UNIVERSITY R&DB FOUNDATION, Seoul (KR)

(72) Inventors: Kwang Gi Kim, Seoul (KR); Jeong Min Hwang, Gyeonggi-do (KR); Hee Kyung Yang, Gyeonggi-do (KR); Sang Beom Han, Gyeonggi-do (KR); Ji Eun Oh, Gyeonggi-do (KR)

(73) Assignees: NATIONAL CANCER CENTER, Gyongg-do (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 63 days.

(21) Appl. No.: 15/110,686

(22) PCT Filed: Jan. 7, 2015

(86) PCT No.: PCT/KR2015/000131
§ 371 (c)(1),
(2) Date: Jul. 8, 2016

(87) PCT Pub. No.: WO2015/105324
PCT Pub. Date: Jul. 16, 2015

(65) Prior Publication Data
US 2016/0324413 A1    Nov. 10, 2016

(30) Foreign Application Priority Data

Jan. 10, 2014 (KR) .................. 10-2014-0003543

(51) Int. Cl.
| | |
|---|---|
| *G06K 9/00* | (2006.01) |
| *A61B 3/00* | (2006.01) |
| *A61B 3/12* | (2006.01) |
| *A61B 3/14* | (2006.01) |
| *G06T 7/00* | (2017.01) |

(52) U.S. Cl.
CPC .............. *A61B 3/0025* (2013.01); *A61B 3/12* (2013.01); *A61B 3/14* (2013.01); *G06T 7/0012* (2013.01); *G06T 2207/20061* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 8,355,544 B2 * | 1/2013 | Gomez-Ulla de Irazazabal | G06K 9/0061 351/209 |
| 2003/0228117 A1 * | 12/2003 | Truitt | A61B 3/14 385/122 |

(Continued)

*Primary Examiner* — Hadi Akhavannik
(74) *Attorney, Agent, or Firm* — Porzio Bromberg & Newman P.C.

(57) ABSTRACT

The present invention relates to a method for detecting a defective zone of a retinal nerve fiber layer (hereinafter, referred to as a RNFL), wherein a green channel image is extracted from an acquired fundus image, and polar coordinate conversion is conducted with reference to the center of a detected optic disc with regard to the image, thereby detecting a defective area of the RNFL.

7 Claims, 6 Drawing Sheets

(56) References Cited

U.S. PATENT DOCUMENTS

| | | | | |
|---|---|---|---|---|
| 2007/0263227 A1* | 11/2007 | Mujat | ............... | A61B 3/102 |
| | | | | 356/511 |
| 2009/0268159 A1* | 10/2009 | Xu | ............... | A61B 3/102 |
| | | | | 351/206 |
| 2012/0177262 A1* | 7/2012 | Bhuiyan | ............... | A61B 3/0025 |
| | | | | 382/128 |
| 2013/0215388 A1* | 8/2013 | Imamura | ............... | G06T 7/0012 |
| | | | | 351/206 |

* cited by examiner (a)

(b)

(c)

(d)

(a)

(b)

(a)

(b)

(c)

(a)

(a)          (b)

METHOD FOR DETECTING DEFECTIVE ZONE OF RETINAL NERVE FIBER LAYER

TECHNICAL FIELD

The present invention relates to a method for detecting a defective zone of a retinal nerve fiber layer (hereinafter, referred to as a RNFL), wherein a green channel image is extracted from an acquired fundus image, and polar coordinate conversion is conducted with reference to the center of a detected optic disc with regard to the image, thereby detecting a defective area of the RNFL.

BACKGROUND OF THE INVENTION

Glaucoma is a progressive disease that begins with structural damage of optic nerve and RNFL and leads to visual field damage. Glaucoma is a progressive disease that begins with structural damage of optic nerve and RNFL and leads to visual field damage. In terms of treatment, detecting glaucomatous visual field loss or progression of visual field defect in early stage is very important because the glaucoma is an irreversible disease. In particular, in the case of chronic progression of the glaucoma, identifying determination as soon as possible whether the glaucoma is progressed or not is important because there are not any particular symptoms in most cases.

In order to diagnose the glaucoma accurately, a number of tests are required. For example, in order to diagnose the glaucoma, tonometry that measures degree of intraocular pressure, test for optic nerve and optic nerve fiber layer that measures whether the optic nerve is damaged and its degree, visual field test that evaluates vision disturbance according to the optic nerve damage, and gonioscopy that finds reason in the case that the present intraocular pressure is high or factor that may be risen hereafter even though the intraocular pressure is not high are required.

However, above glaucoma diagnosis test takes a lot of time because it is performed through various procedures, hence in the case of glaucoma diagnosis patients get to feel fatigue a lot.

DETAILED DESCRIPTION OF THE INVENTION

Technical Problem

The present disclosure is originated to solve the problem and is directed to providing a method for detecting the defective zone of RNFL which enables to detect rapidly and simply whether the RNFL is defected by the glaucoma compared to the related art through the acquired fundus image of patient.

Solution to Problem

The method for detecting the defective zone of the RNFL according to an aspect of the present disclosure may include: a fundus image acquisition stage that acquires a fundus image of removed blood vessel zone; a detecting center of the optic disc stage that detects the center of the optic disc with regard to the image; a polar coordinate conversion stage that is converted based on the detected center of the optic disc; and a detecting an atrophy zone stage that detects the atrophy zone by conducting Hough transformation related with an image that converted into polar coordinate.

The fundus image acquisition stage may include: a green channel image extracting stage that extracts from the acquired fundus image; a brightness correcting stage that corrects brightness non-uniformly regarding the acquired green channel image; and a removing blood vessel zone stage that removes the blood vessel zone among the acquired fundus images.

Removing noise information stage that removes the noise information regarding the extracted green channel image from the green channel image extracting stage may further include.

In regards to the removing noise information stages, it enables to remove noise by applying mask image through a morphological operation and a median filter.

In regards to the brightness correcting stage, it enables to reverse estimate a bias image which is information of shading artifact by using the green channel image that extracted from the extracting green channel image, and remove the bias image in the green channel image.

In regards to the removing blood vessel zone, it enables to remove the extracted blood vessel zone by applying a bottom hat method and a kirsch method repeatedly.

In regards to the detecting atrophy zone, it enables to detect the atrophy zone by applying Gaussian filter and conducting Hough transformation regarding a detected canny edge image.

Removing false positive zone that removes the detected false positive zone in the detecting atrophy zone stage may further include.

In regards to the removing false positive stage, it enables to remove a zone which is greater than regular macular, blood vessel zone, and intensity among the detected atrophy zone from the detecting atrophy zone stage.

Advantageous Effects of Invention

The method for detecting the defective zone of RNFL according to the exemplary embodiment of the present disclosure is capable of extracting the green channel image that appears the damage of the RNFL and blood vessel contrast the most excellently among the acquired fundus image by the patient and detecting the defective zone of RNFL through the polar coordinate conversion based on the center of the detected optic disc with regard to the image, thereby having an effect of detecting easily whether or not the glaucoma is occurred compared to the related art.

MODES FOR CARRYING OUT THE INVENTION

The present disclosure may be applied various conversion and have various exemplary embodiments, therefore, certain exemplary embodiments are to be illustrated and detailed description will be described. However, it will not necessarily limited to certain modes for carrying of the present invention, and needs to be understood that it includes all conversion included idea of the present invention and technical range and equivalents or substitutes. In description of the present disclosure, detailed description will be skipped in the case that it is determined the detailed description regarding related prior art may cloud substance of the present disclosure.

Terms such as "the first", "the second" etc., which may be used to describe various elements, however, the elements should not be construed as being limited to the terms. The terms are used only for distinguishing between an element and other elements. The terms used in the present application are used only for description of certain exemplary embodiment but the terms are not intended to limit the present disclosure. The terms used in the present application are used only for description of certain exemplary embodiment but the terms are not intended to limit the present disclosure. The terms used in the present application are used only for description of certain exemplary embodiment but the terms are not intended to limit the present disclosure. Description of plural is included unless description of singular is intended to signify differently. In the present application, terms "include" or "have" etc., are to be intended to designate presence of feature, number, stage, element, component or combination of them which are described in the specification but one or greater than the features, the number, the stage, the element, the component, or the presence of their combination or additional possibility are needed to understand they are not excluded in advance.

The present disclosure will be described more fully hereinafter with reference to the accompanying drawings, in which exemplary embodiments of the invention are shown.

Figure 1:
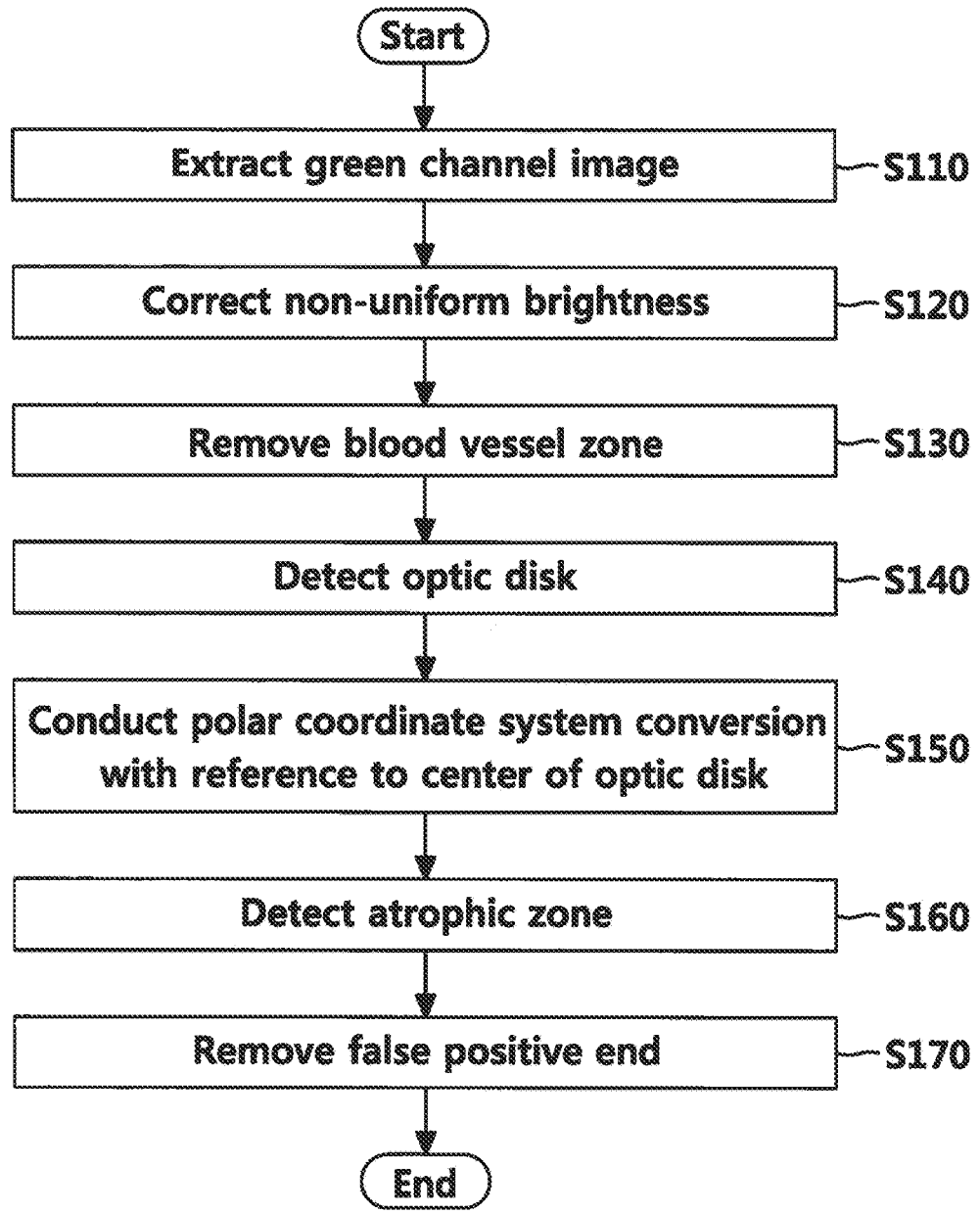
FIG. 1 shows a flowchart of the method for detecting the defective zone of the RNFL according to an exemplary embodiment of the present disclosure.

FIG. 1 shows a flowchart of the method for detecting the defective zone of the RNFL according to the exemplary embodiment of the present disclosure.

As illustrated in FIG. 1, the method for detecting the defective zone of the RNFL according to practical exemplary embodiment of the present disclosure may include: the fundus image acquisition stage that acquires the fundus image of the removed blood vessel zone; the detecting center of the optic disc stage that detects the center of the optic disc with regard to the image; the polar coordinate conversion stage that is converted based on the detected center of the optic disc; and the detecting an atrophy zone stage that detects the atrophy zone by conducting Hough transformation related with an image that converted into polar coordinate. In this case, the fundus image acquisition stage may include: the green channel image extracting stage that extracts from the acquired fundus image; the brightness correcting stage that corrects the brightness non-uniformly regarding the acquired green channel image; and the removing blood vessel zone stage that removes the blood vessel zone among the acquired fundus images. Particularly, the removing noise information stage that removes the noise information regarding the extracted green channel image from the green channel image extracting stage may further include.

Detailed image processing according to each stage and result of same will be described with reference to FIG. 2 to FIG. 12.

First, acquire the fundus image in order to detect whether to the RNFL is damaged. The fundus image may be acquired using digital fundus camera and various acquiring image apparatus. Practically, fundus image having color may be acquired through the digital fundus camera.

The method for detecting the defective zone of the RNFL according to the present disclosure extracts the green channel among the acquired fund images through the method thereof. (S110) Particularly, the RGB channel regarding the acquired color fundus image extracts is segmented and the only green channel image is extracted.

Figure 2:
FIG. 2 shows a drawing of an extracted image by RGB channels regarding the acquired fundus image.
Figure 2:
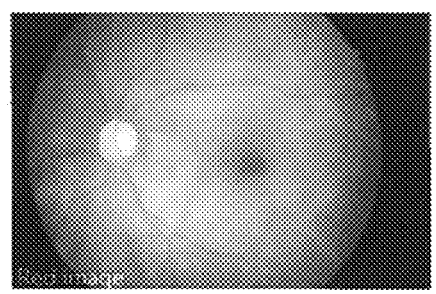
Figure 2:
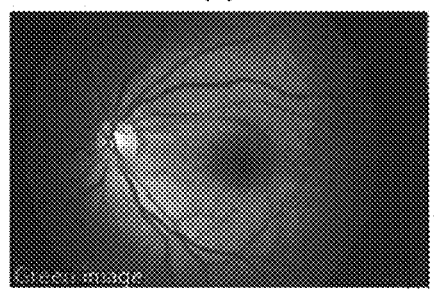
Figure 2:
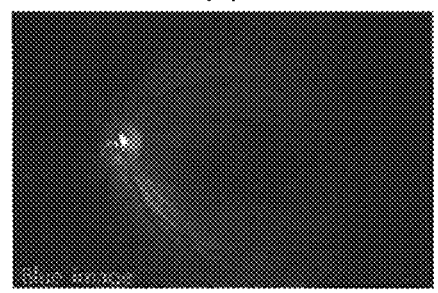

FIG. 2 shows the drawing of the extracted image by RGB channels regarding the acquired fundus image, and result of extracting the fundus image by RGB channels is illustrated in a S110 stage. In FIG. 2, (a) shows the extracted fundus image, (b) shows a red image of extracted red channel, (c) shows a green image of extracted green channel, and (d) shows a blue image of extracted blue channel. The green channel image illustrated in (c) shows more excellently damage of the RNFL and the blood vessel zone contrast than among the red image, green image, and blue image. Accordingly, in the S110 stage, the green channel image information is extracted and used.

Selectively, noise may be removed regarding extracted green channel image in the S110 stage. Particularly, the noise is removed regarding the extracted green channel image in the S110 stage by applying the mask image through the morphological operation and the median filter. Text and the noise information that are presented in a background image of the fundus image may be removed through the method thereof.

Figure 3:
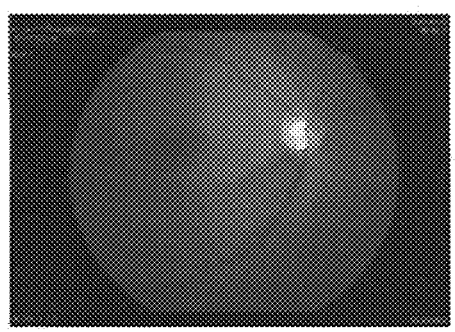
FIG. 3 illustrates a drawing of a fundus image before and after removing text and the noise information.
Figure 3:
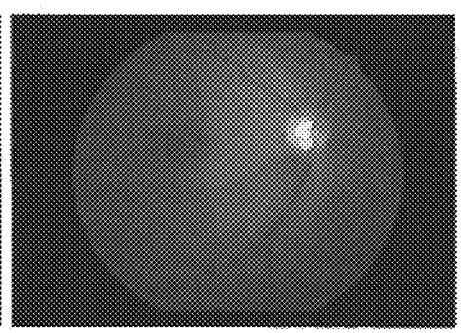

FIG. 3 illustrates the drawing of the fundus image before and after removing the text and the noise information. (a) in FIG. 3 shows an image before removing the text and the noise information regarding the extracted green channel image in the S110 stage thereof, (b) shows an image after removing the text and the noise information. As described above, an unnecessary information to be removed the RNFL zone may be removed through the removing noise.

The brightness is corrected non-uniformly regarding the extracted green channel image in the S110 stage thereof (S120) Practically, the brightness regarding the removed image of the text and the noise information is corrected non-uniformly through the method thereof in the S120 stage.

In general, brightness of the fundus image becomes non-uniform because image photographing condition of retinal and hemispherical feature. The non-uniformed brightness may influence henceforward on removing the blood vessel zone and detecting the defective zone of the RNFL, hence correction on this is needed.

In the present disclosure, a method for correction the brightness using the bias image is used in order to correct the non-uniformed brightness. In this case, an acquired image is defined as multiplication of a bias image b and an ideal, I image.

$$G(i,j)=B(i,j)\times I(i,j) \qquad \text{MATHEMATICAL FORMULA 1}$$

In this case, i, j means pixel position in the image, G is a green channel image acquired in the S110 stage (practically, removing noise image regarding the acquired green channel image in the S110 stage), and an ideal image in this case means a uniformed brightness image. Accordingly, following FIG. 4 is each image information.

Figure 4:
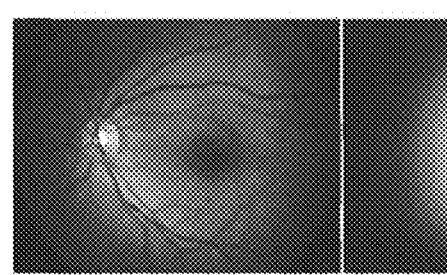
FIG. 4 shows a drawing of a green channel image, a reversely estimated bias image from the green channel image, and a removed bias image from the green channel image.
Figure 4:
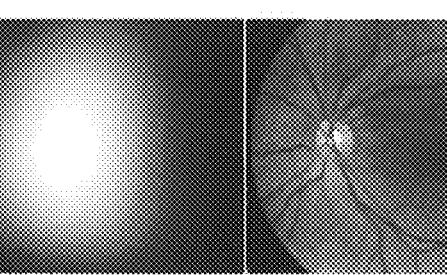
Figure 4:
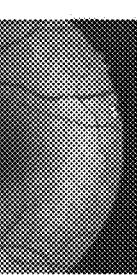

FIG. 4 shows the drawing of the green channel image, the reversely estimated bias image from the green channel image, and the removed bias image from the green channel image. In FIG. 4, (a) is the green channel image, (b) is the reversely estimated bias image from the image (a), and (c) is the removed image (b) information image from the image (a). In this case, a bright corrected image is acquired by reversely estimating the bias image which is shading artifact using the green channel image, removing the reversely estimated bias image from the green channel image.

Figure 5:
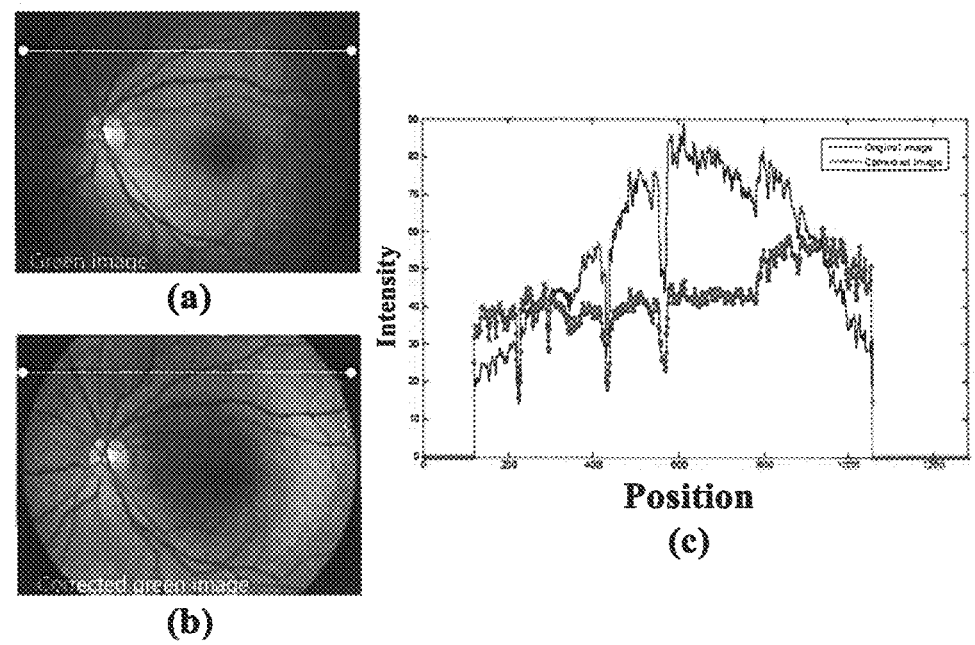
FIG. 5 shows a drawing of brightness corrected non-uniformly result.

FIG. 5 shows the drawing of the brightness corrected non-uniformly result. In FIG. 5, (a) shows a green channel image (green image), (b) shows non-uniformly corrected brightness image regarding the image (a) (corrected green image), and (c) illustrates intensity of the images before and after correction. Referring to the result, in the non-uniformly corrected brightness image (b), generally uniformed intensity of the image may be checked. In contrast an original image (cited as thin lines) cited in (c) has non-uniformed intensity by position, relatively uniformed intensity by position in a corrected image (cited as bold lines) may be checked.

The blood vessel zone in the uniformed brightness image is removed through the S120 stage. (S130) This is for detecting the defective zone of the RNFL effectively.

In an applicable exemplary embodiment of the present disclosure, the S130 stage enables to remove extracted blood vessel zone by applying the bottom hat method which is the morphological operation and the kirsch method which is one of edge detection method repeatedly.

First, in an exemplary embodiment of the present disclosure, as a structure element (hereinafter, referred to as a SE) having bottom hat method that applied to the S130 stage, SE having 20 pixel diameter disc type may be used. That is, a morphological filtering operation may be conducted using the SE. However, size of the SE is an applied value of representative fundus image profile measurement result, the size of the SE may be applied by modifying according to an exemplary application.

Kirsch filter which is applied to the kirsch method in the present disclosure is a filter using eight-way filter, and each way is north, northwest, west, southwest, south, southeast, east, and northeast.

Figure 6:
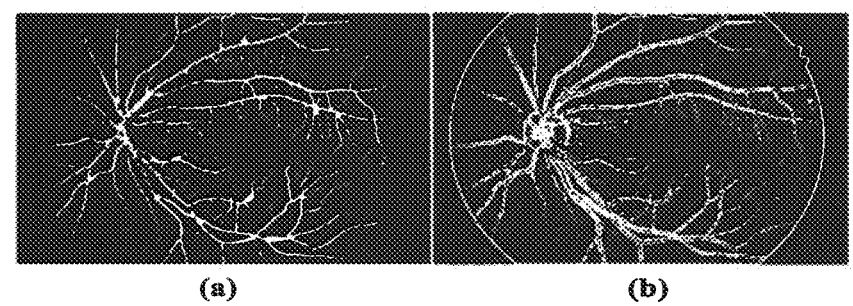
FIG. 6 shows a drawing of detection result of the blood vessel according to the bottom hat method and the kirsch method.

FIG. 6 shows the drawing of the detection result of the blood vessel according to the bottom hat method and the kirsch method, That is, (a) in FIG. 6 is a drawing of the detection result of the blood vessel according to the bottom hat method, and (b) is the detection result of the blood vessel according to the kirsch method. In comparison with both results, the result of the blood vessel is different according to each method.

Accordingly, the present disclosure characterizes detecting the blood vessel zone by applying the bottom hat method and the kirsch method repeatedly in order to supplement weakness of both methods.

Figure 7:
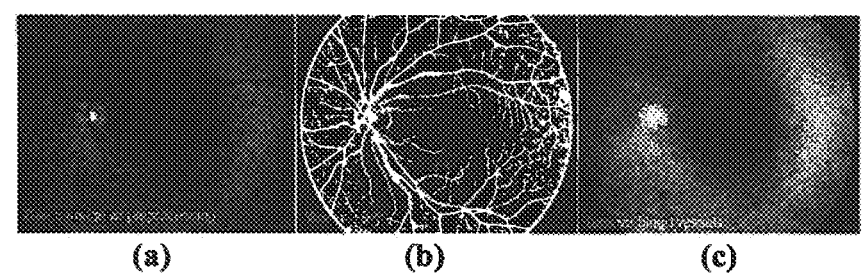
FIG. 7 shows a drawing of a pretreated green channel image, finally detected blood vessel zone, and an image removed blood vessel zone from the green channel image.

Blood vessel zone information which is finally detected according to the method and fundus image information removed it as following FIG. 7.

FIG. 7 shows the drawing of the pretreated green channel image, the finally detected blood vessel zone, and the image removed blood vessel zone from the green channel image. In FIG. 7, (a) illustrates the pretreated green channel image, (b) is the finally detected blood vessel zone through the above method, and (c) is the image removed the image (b) information from the image (a).

As described above, the present disclosure characterizes detecting the blood vessel zone more perfectly by applying repeatedly the bottom hat method and the kirsch method in order to detect the final blood vessel zone.

The center of the optic disc with regard to the image removed the blood vessel zone is detected through the S130 stage. (S140) In the S140 state the optic disc of the fundus image may be detected the center of the optic disc using optic disc characteristic having more bright value against periphery. To do this, local maximum method which is robust to noise may be applied.

Additionally, the macular of the fundus image may be detected center of the macular using macular characteristic having dark value against periphery. To do this local minimum method which is robust to noise may be applied.

Figure 8:
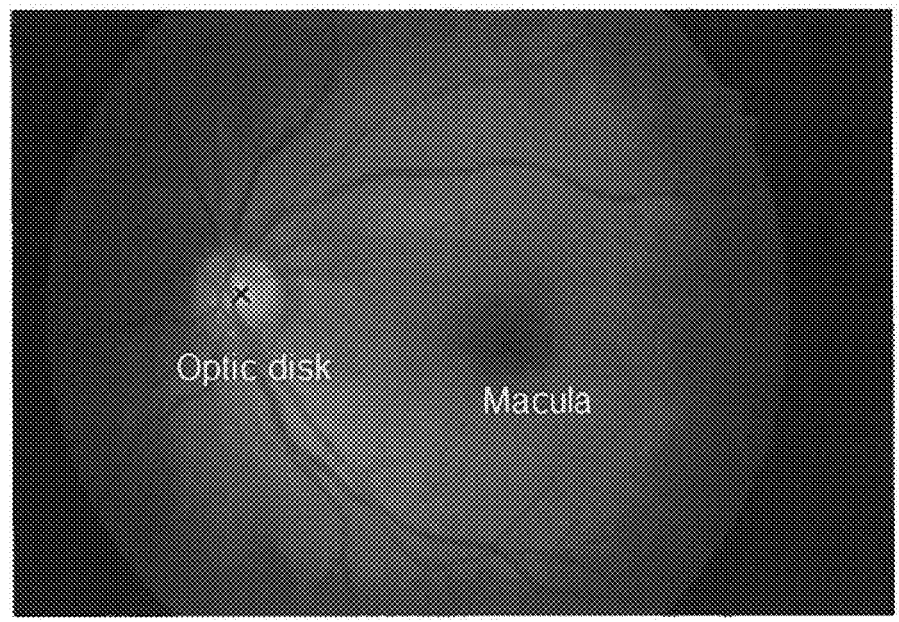
FIG. 8 shows a drawing of a detected image of the optic disc and center of the macular.

FIG. 8 shows the drawing of the detected image of the optic disc and center of the macular. As cited in FIG. 8, the optic dis and the macular may be detected using the above method. In FIG. 8 the optic disc detected through the above method and the center of the macular may be indicated respectively as "X", however, the coordinate information may be indicated with various indicating methods.

Accordingly, the polar coordinate conversion is conducted with reference to the center of the detected optic disc in the S140 stage. (S150)

In general, the defective zone of the RNFN is indicated radially from the center of the optic disc, and form may be showed variously such as fan-shaped, wedge-shaped, slit-like, spindle-like etc. Accordingly, in the present disclosure the polar coordinate conversion is conducted based on the center of the optic disc in order to detect the defective zone of RNFN having various forms more effectively.

Figure 9:
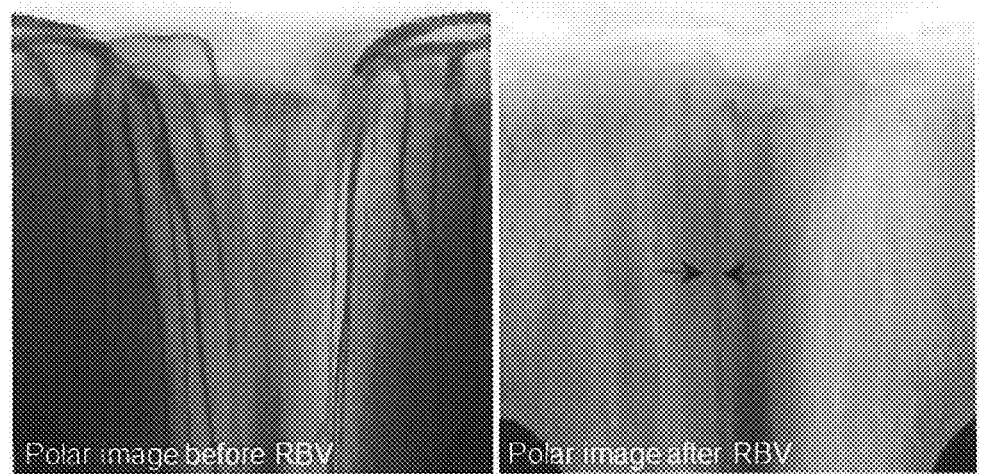
FIG. 9 shows a drawing of an image before and after removing the blood vessel zone in the image that converted into the polar coordinate based on the center of the optic disc.

FIG. 9 shows the drawing of the image before and after removing the blood vessel zone in the image that converted into the polar coordinate based on the center of the optic disc.

In FIG. 9, (a) is the image of removing the blood vessel zone and (b) is the image of after removing the blood vessel zone. As described above, the present disclosure enables to detect the defective zone of the RNFL effectively by removing the blood vessel zone, and the defective zone of the RNFL is transformed into an almost vertical direction line form can be checked.

The atrophy zone is detected by conducting the Hough transformation related with an image that converted into polar coordinate through the S150 stage. (S160) More practically, the atrophy zone may be detected after applying the Gaussian filter in order to smooth detected blood vessel zone boundaries, and by conducting Hough transformation regarding the detected canny edge image that corrects discontinued edge.

Figure 10:
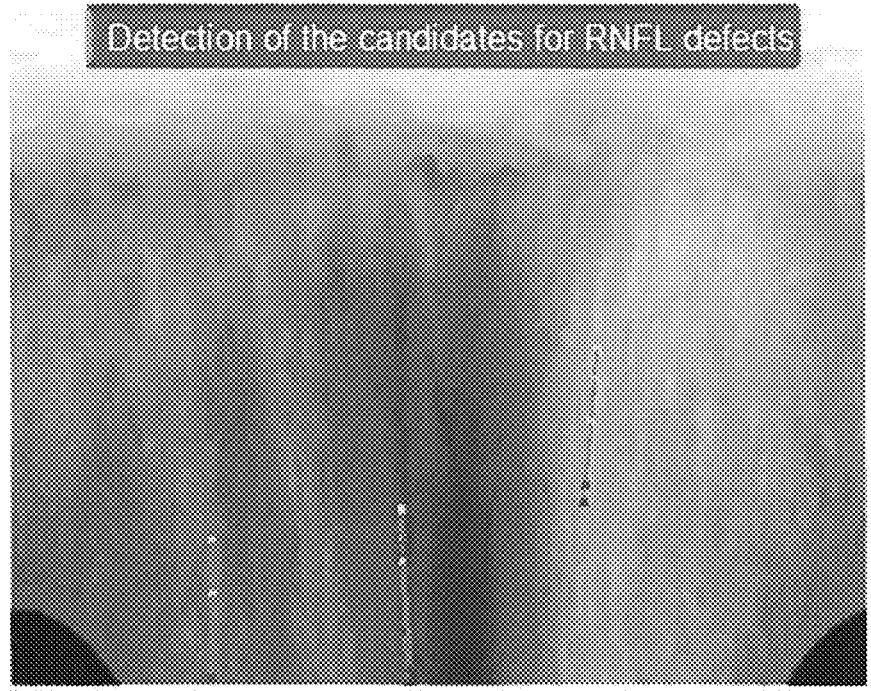
FIG. 10 shows a drawing of detection result of the atrophy zone in the RNFL.

FIG. 10 shows the drawing of the detection result of the atrophy zone in the RNFL. As described above, the atrophy zone detected through the S160 stage may be illustrated in FIG. 10.

In this case, wrong detected atrophy may be included the atrophy zone detected through the S160 stage. Accordingly, the false positive zone in the atrophy zone detected through the S160 stage may be further removed. (S170)

In terms of anatomical feature of the RNFL, in the defective zone of the RNFL which would be detected through the present disclosure the macular and the blood vessel zone are not included, and high intensity image zone is not included.

Using the above feature, in the S170 stage, the zone which is greater than regular macular, blood vessel zone, and intensity among the detected atrophy zone from the S160 stage may be removed by detecting as the false positive zone. In this case, a reference value which is to detect whether it is applied to the false positive zone is set by user, or a reference value which is applicable to ordinary patients may be applied.

Figure 11:
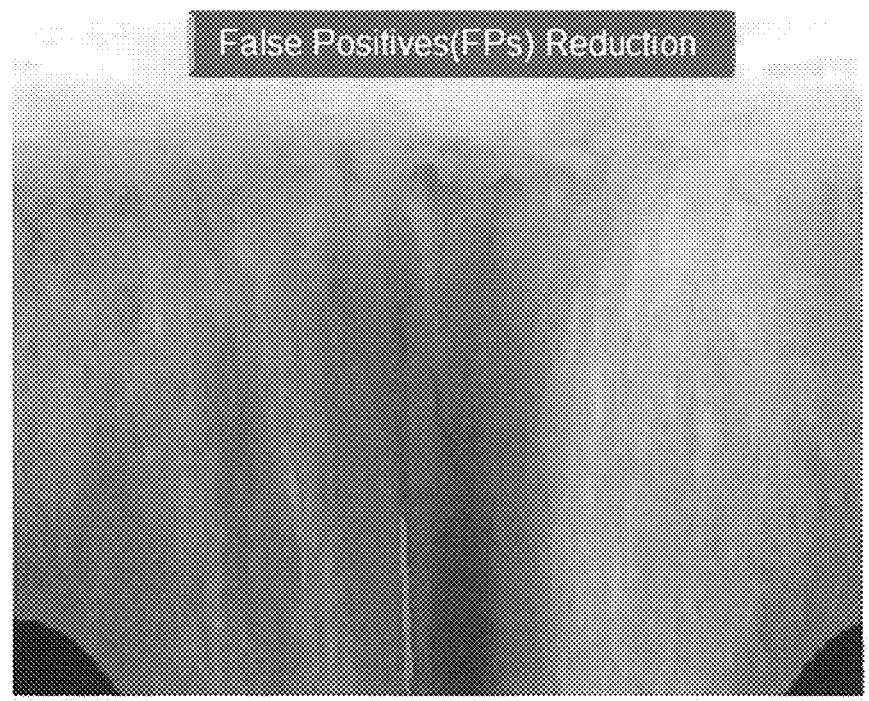
FIG. 11 shows a drawing of a result removing false positive.
Figure 12:
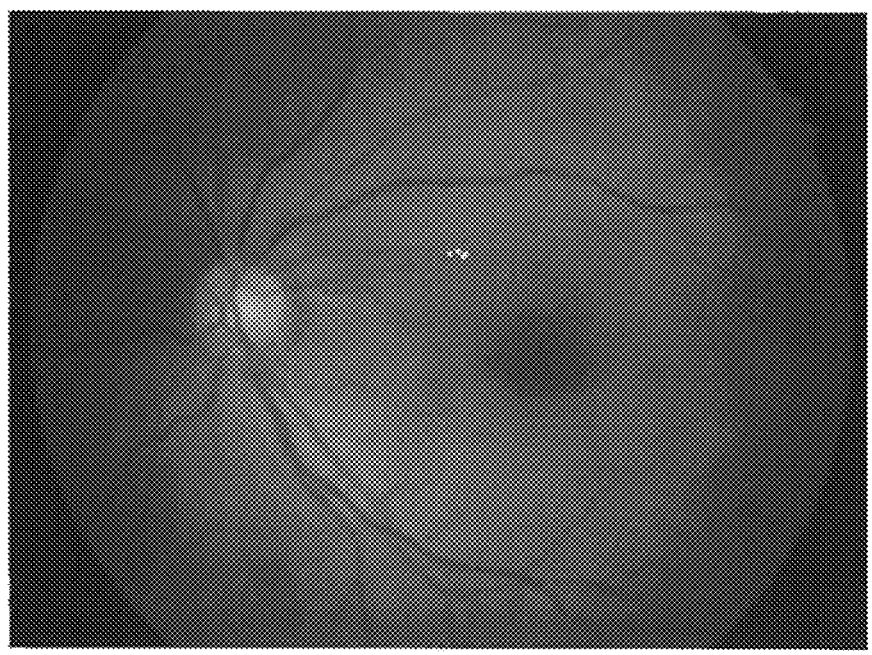
FIG. 12 shows a drawing of a final result of the defective zone of the RNFL according to the present disclosure.

FIG. 11 shows the drawing of the result removing false positive, and FIG. 12 shows the drawing of the final result of the defective zone of the RNFL according to the the present disclosure.

That is, as cited in FIG. 11, more definite image information may be acquired by removing the false positive zone through the S170 stage. Information of the defective zone of the RNFL acquired as the above may be appeared in the fundus image as FIG. 12.

Simulation result regarding the method for detecting the defective zone of the RNFL is as follows. Simulation regarding the present disclosure is conducted for 19 patients who have damage degree of the RNFL in early stage, and simulation regarding 31 defective lesions of the RNFL included the fundus image is conducted. The fundus image is photographed using a fundus camera KOWA VX-10 having a digital camera, Nikon D80, with 24 bit color image which is valued 1278*948 resolution.

Result of the simulation will be described more fully hereinafter through the FIG. 13.

Figure 13:
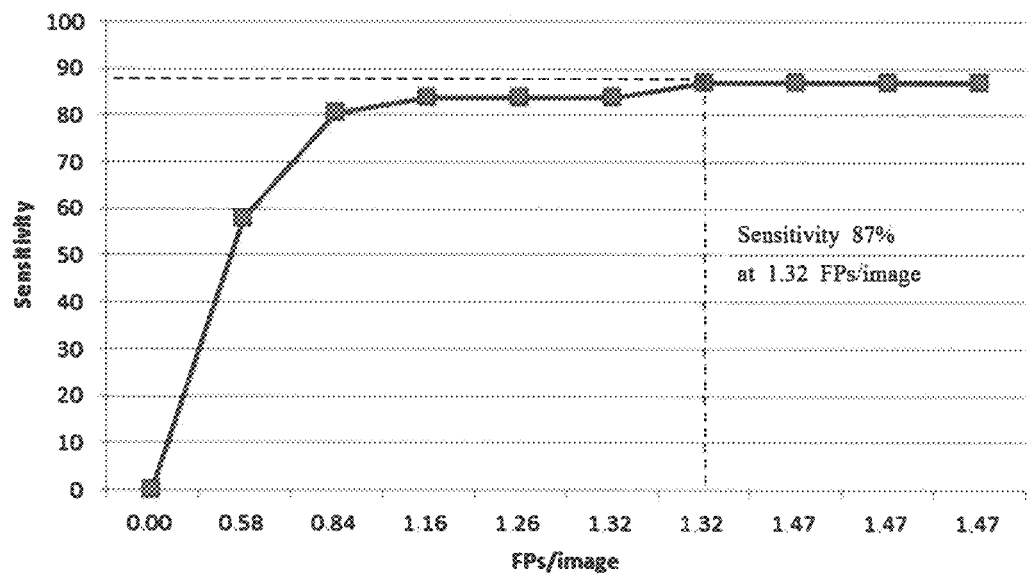
FIG. 13 shows a drawing of sensitivity and FPs/image rate regarding the defective zone of the RNFL according to the exemplary embodiment of the present disclosure.

FIG. 13 shows the drawing of the sensitivity and the FPs/image rate regarding the defective zone of the RNFL according to the exemplary embodiment of the present disclosure.

As cited in FIG. 13, as a result of evaluating 19 fundus images, 87 percent of sensitivity are shown, and the FPs/image rate is confirmed as 1.32 FPs/image.

As described above, the method for detecting the defective zone of the RNFL according to the present disclosure may be effective in detecting the defective zone of the RNFL through the polar coordinate conversion with regard to the fundus image, thereby having the effect of detecting easily whether or not the glaucoma is occurred compared to the related art.

Hitherto, the present disclosure has been described based on the practical exemplary embodiments. Those skilled in the art are to be understood that the present disclosure may be embodied in modified form within scope of essential feature of the present disclosure. Therefore, exemplary embodiment of the present disclosure described herein should be considered from expository point of view, and should not be considered from limited point of view. Range of the present disclosure is shown in spirit and scope of appended claims, not in the above-described description, and every difference within equivalent range should be construed as being included in the present disclosure.

What is claimed is:

1. A method for detecting a defective zone of a retinal nerve fiber layer comprising:
   a fundus image acquiring stage that acquires a fundus image of removed blood vessel zone;
   a detecting center of the optic disc stage that detects the center of the optic disc with regard to the image;
   a polar coordinate converting stage that is converted based on the detected center of the optic disc; and
   a detecting an atrophy zone stage that detects the atrophy zone by conducting Hough transformation related with an image that converted into polar coordinate,
   wherein the fundus image acquiring stage comprises, a green channel image extracting stage that extracts from the acquired fundus image; a brightness correcting stage that corrects non-uniformly regarding the acquired green channel image; and a removing blood vessel zone stage that removes the blood vessel zone among the acquired fundus images and wherein the brightness correcting stage comprises, reverse estimating a bias image which is information of shading artifact by using the green channel image that extracted from the extracting green channel image, and removing the bias image in the green channel image.

2. The method for detecting the defective zone of the retinal nerve fiber layer of claim 1, further comprising, the removing noise information stage that removes the noise information regarding the extracted green channel image from the green channel image extracting stage.

3. The method for detecting the defective zone of the retinal nerve fiber layer of claim 2, wherein the removing noise information stage comprises removing noise by applying mask image through a morphological operation and a median filter.

4. The method for detecting the defective zone of the retinal nerve fiber layer of claim 1, wherein the removing blood vessel zone stage comprises removing extracted blood vessel zone by applying a bottom hat method and a kirsch method repeatedly.

5. The method for detecting the defective zone of the retinal nerve fiber layer of claim 1,
   wherein the detecting an atrophy zone stage comprises,
   detecting the atrophy zone by applying Gaussian filter,
   and conducting Hough transformation regarding a detected canny edge image.

6. The method for detecting the defective zone of a retinal nerve fiber layer of claim 1, further comprising, the removing false positive zone that removes the detected false positive zone in the detecting atrophy zone stage.

7. The method for detecting the defective zone of a retinal nerve fiber layer of claim 6,
   the removing false positive zone comprises,
   removing a zone which is greater than regular macular, blood vessel zone, and intensity among the detected atrophy zone from the detecting atrophy zone stage.

* * * * *